United States Patent
Burgfels et al.

(10) Patent No.: US 9,174,204 B2
(45) Date of Patent: Nov. 3, 2015

(54) CATALYST BASED ON ZEOLITE FOR PRODUCING OLEFINS AND FOR OLIGOMERIZING OLEFINS

(75) Inventors: Götz Burgfels, Bad Aibling (DE); Stefan Klingelhöfer, Rosenheim (DE); Lay Hwa Ong, Amsterdam (NL); Roberta Olindo, Frankfurt am Main (DE); Johannes A. Lercher, Ottobrunn (DE); Friedrich Schmidt, Rosenheim (DE)

(73) Assignee: SUD-CHEMIE IP GMBH & CO. KG, Munich (DE)

( * ) Notice: Subject to any disclaimer, the term of this patent is extended or adjusted under 35 U.S.C. 154(b) by 567 days.

(21) Appl. No.: 13/575,054

(22) PCT Filed: Jan. 26, 2011

(86) PCT No.: PCT/EP2011/051023
§ 371 (c)(1),
(2), (4) Date: Nov. 15, 2012

(87) PCT Pub. No.: WO2011/092177
PCT Pub. Date: Aug. 4, 2011

(65) Prior Publication Data
US 2013/0053609 A1  Feb. 28, 2013

(30) Foreign Application Priority Data

Jan. 26, 2010 (DE) .................. 10 2010 005 704

(51) Int. Cl.
| | |
|---|---|
| *B01J 29/06* | (2006.01) |
| *B01J 29/40* | (2006.01) |
| *C07C 11/02* | (2006.01) |
| *B01J 35/10* | (2006.01) |
| *C07C 1/20* | (2006.01) |
| *C07C 2/12* | (2006.01) |
| *C10G 50/00* | (2006.01) |
| *C10G 3/00* | (2006.01) |

(52) U.S. Cl.
CPC *B01J 29/40* (2013.01); *B01J 29/06* (2013.01); *B01J 35/1019* (2013.01); *C07C 1/20* (2013.01); *C07C 2/12* (2013.01); *C07C 11/02* (2013.01); *C10G 3/49* (2013.01); *C10G 50/00* (2013.01); *B01J 2229/42* (2013.01); *C07C 2529/40* (2013.01); *C07C 2529/70* (2013.01); *C10G 2400/20* (2013.01)

(58) Field of Classification Search
CPC ........ B01J 29/06; B01J 29/40; B01J 35/1019; B01J 2229/42; C07C 1/20; C07C 2/12; C07C 11/02; C07C 11/06; C07C 11/08; C07C 2529/40; C10G 3/49; C10G 50/00; C10G 2400/20
See application file for complete search history.

(56) References Cited

U.S. PATENT DOCUMENTS

| | | | |
|---|---|---|---|
| 4,058,576 | A | 11/1977 | Chang et al. |
| 4,471,150 | A | 9/1984 | Wu |
| 5,063,187 | A | 11/1991 | Burgfels et al. |
| 5,672,800 | A | 9/1997 | Mathys et al. |
| 7,015,369 | B2 | 3/2006 | Hack et al. |
| 7,229,941 | B2 | 6/2007 | Burgfels et al. |
| 7,459,412 | B2 | 12/2008 | Lercher et al. |
| 2004/0181108 | A1* | 9/2004 | Lercher et al. ............... 585/722 |
| 2008/0222945 | A1* | 9/2008 | Hara et al. .................... 44/300 |
| 2010/0063337 | A1 | 3/2010 | Bach et al. |
| 2013/0053609 | A1* | 2/2013 | Burgfels et al. ............... 585/533 |

FOREIGN PATENT DOCUMENTS

| | | |
|---|---|---|
| DE | 10027159 A1 | 12/2001 |
| EP | 0448000 A1 | 9/1991 |
| WO | 9522516 | 8/1995 |
| WO | 2009071654 A1 | 6/2009 |

OTHER PUBLICATIONS

Bjorgen, M., et al., Methanol to gasoline over zeolite H-ZSM-5: Improved catalyst performance by treatment with NaOH, Applied Catalysis A: General 345, 43-50 (2008).

Yamazaki, H., et al., Evidence for a "Carbene-like" intermediate during the reaction of methoxy species with light alkenes on H-ZSM-5, Angewantde Chemie. International Edition 50:8, 1853-1856 (2011).

* cited by examiner

*Primary Examiner* — David M Brunsman
(74) *Attorney, Agent, or Firm* — Anthony A. Bisulca

(57) ABSTRACT

The invention relates to a novel catalyst based on zeolite, the production of that catalyst, and the use of the catalyst in a method for producing lower olefins from oxygenates and for oligomerizing olefins. The novel catalyst has a $SiO_2/Al_2O_3$ weight ratio of 2 to 9, a BET surface of 250 to 500 m²/g, and an Na content under 200 ppm. The catalyst includes a crystalline alumosilicate zeolite and a binder. The catalyst is characterized in that the ratio of the peak heights of its IR absorption bands $v=3610\ cm^{-1} \pm 20\ cm^{-1}/v=3680\ cm^{-1} \pm 20\ cm^{-1}$ is greater than 1.8.

9 Claims, 1 Drawing Sheet

Propene selectivity as a function of the reaction duration

Methanol conversion as a function of the reaction duration

CATALYST BASED ON ZEOLITE FOR PRODUCING OLEFINS AND FOR OLIGOMERIZING OLEFINS

This application is a 371 filing of PCT/EP2011/051023, filed Jan. 26, 2011.

The present invention relates to novel zeolite-based catalysts, as well as their use in a process for producing low olefins from oxygenates and in a process for oligomerizing olefins.

The conversion of oxygenates, in particular methanol or dimethyl ether, to low olefins, in particular propylene, has been known for a long time. Crystalline aluminosilicates are often used as catalysts in the process. The production of propylene is of great commercial interest as propylene is an important raw material for obtaining polypropylene, wherein the propylene obtained from methanol is preferable to the propylene obtained by the thermal splitting of hydrocarbons, as it is virtually free of sulphur compounds.

Such a process is known from U.S. Pat. No. 4,058,576. In detail, in a first stage in this process methanol is converted at least partly to dimethyl ether using an acid catalyst, such as gamma-aluminium oxide, in an exothermic condensation reaction. In this way, part of the reaction heat of the conversion of the methanol to low olefins, carried out in the second stage, can be removed, as the heat produced during the exothermic conversion is less when using dimethyl ether as starting material than when using methanol. In the second stage, the conversion takes place via a crystalline ZSM-5-type zeolite. This is a crystalline aluminosilicate of the pentasil type with a ratio of silica to aluminium of at least 12, a constraint index of 1 to 12 and a pore size greater than 0.5 nm.

The conversion in the second stage takes place in a tubular reactor, wherein preferably olefins with three or more carbon atoms ($C_{3+}$ olefins) are obtained as low olefins. These low olefins are then converted under specific operating conditions using the ZSM-5 catalyst to hydrocarbons in the light gasoline boiling-point range. The proportion of $C_{3+}$ olefins and gasoline depends on the reaction conditions. However, the conversion is preferably carried out at high pressure so that the reactor volume is better utilized.

A similar process is known from U.S. Pat. No. 4,471,150. In this process, a crystalline aluminosilicate modified with magnesium oxide, manganese oxide or magnesium oxide/platinum oxide, e.g. a ZSM-34-type zeolite in the H form with a relatively high alkali content (350 ppm Na, 1.47% K), is used. The conversion of the methanol and/or dimethyl ether steam can be carried out in a fixed bed or in a fluidized bed with diluents such as steam, wherein preferably more than 0.5 mol water per mol organic reactants is used. The total pressure is preferably to be between approximately 0.37 and 3.0, wherein atmospheric pressure is particularly preferably used. The propylene content of the produced olefin mixture is merely between 21 and 29 wt.-%.

A process is known from EP 0 448 000 A1 in which, to produce an olefin mixture with at least 5 wt.-% ethylene, at least 35 wt.-% propylene and at most 30 wt.-% butylene, relative to the total hydrocarbons, the conversion is carried out under the following conditions: (a) at a total pressure of from 10 to 90 kPa, (b) at a weight ratio between water and methanol or methanol equivalents of from 0.1 to 1.5, (c) at a temperature of the reactor cooling medium of from 280 to 570° C., (d) using a pentasil-type proton-containing catalyst which has an alkali content of less than 380 ppm, a ZnO content of less than 0.1 wt.-%, a CdO content of less than 0.1 wt.-%, a BET surface area of from 300 to 600 m²/g, a primary crystallite size of preferably 0.1 to 0.9 µm and a pore volume of from 0.3 to 0.8 cm³/g.

A pentasil-type catalyst in H form based on crystalline aluminosilicates is known from EP 1 424 128 A1, which is built up from primary crystallites with an average diameter of 0.01 and less than 0.1 µm, which are at least 20% combined to produce agglomerates of from 5 to 500 µm, wherein the catalyst contains peptizable hydrous aluminium oxide as binder in a quantity of from 10 to 40 wt.-%, and wherein the catalyst has a BET surface area of from 300 to 600 m²/g and a pore volume of from 0.3 to 0.8 cm³/g. The catalyst is provided for a use in a CMO process. The selectivity for propylene in the obtained olefin mixture in the examples is approx. 35%.

A pentasil-type catalyst in H form based on crystalline aluminosilicates is known from EP 0 369 364 A2, which is built up from primary crystallites with an average diameter of at least 0.1 and less than 0.9 µm, which are at least 20% combined to produce agglomerates of from 5 to 500 µm, wherein the catalyst contains finely divided aluminium oxide as binder in a quantity of from 10 to 40 wt.-%, and wherein the catalyst has a BET surface area of from 300 to 600 m²/g and a pore volume of from 0.3 to 0.8 cm³/g. The catalyst is provided for a use in a CMO process. The selectivity for $C_2$-$C_4$ olefins of the example is 50 to 55%.

There is still a demand for a catalyst which selectively increases the production of propylene in a process for producing olefins from oxygenates.

This object is achieved according to the invention in that a catalyst which has a $SiO_2/Al_2O_3$ weight ratio of from 2 to 9 and a ratio of the peak heights of the infrared absorption bands $v=3610\pm20$ cm$^{-1}$/$v=3680\pm20$ cm$^{-1}$ of greater than 1.8, preferably greater than 2.0, is provided, wherein the catalyst comprises a crystalline aluminosilicate zeolite and a binder, and has a BET surface area of from 250 to 500 m²/g and a Na content of less than 200 ppm.

Furthermore, the present invention relates to a process for oligomerizing olefins.

The oligomerizing of low olefins, in particular $C_2$-$C_6$ olefins, for producing olefin products with a higher molecular weight is a commercially important process for example within the framework of producing fuel or precursors for plasticizers and surfactants. Crystalline aluminosilicates can also be used as catalysts.

Such a process is known from U.S. Pat. No. 5,672,800. This published document describes a process for oligomerizing a $C_2$-$C_{12}$-alkene-containing feed with a water content of from 0.05 to 0.25 mol-% via a zeolite catalyst selected from TON, MTT, MFI, MTW, EUO and further zeolite structures.

WO 95/22516 describes an olefin-oligomerizing process which consists, under oligomerizing conditions, of bringing an olefin-containing feed into contact with a catalyst comprising at least one zeolite with a constraint index greater than 10, such as e.g. ZSM-22, and at least one zeolite with a constraint index of from 2 to 10, such as e.g. ZSM-5 or ZSM-57, wherein these zeolites are preferably present in a weight ratio of from 10:90 to 90:10. The olefin feed can also contain an inert diluent such as a saturated hydrocarbon.

There is still a demand for a catalyst which selectively increases the yield of the diesel fraction in a process for oligomerizing olefins.

This object is achieved according to the invention in that a catalyst which has a $SiO_2/Al_2O_3$ weight ratio of from 2 to 9 and a ratio of the peak heights of the infrared absorption bands $v=3610\pm20$ cm$^{-1}$/$v=3680\pm20$ cm$^{-1}$ of greater than 1.8, preferably greater than 2.0, is provided, wherein the catalyst comprises a crystalline aluminosilicate zeolite and a binder, and has a BET surface area of from 250 to 500 m$^2$/g and a Na content of less than 200 ppm.

As stated above, the object of the present invention is to provide catalysts comprising aluminosilicate zeolites, which have an increased selectivity in catalytic processes, in particular in a process for producing low olefins from oxygenates, preferably from methanol and/or dimethyl ether, or in a process for oligomerizing olefins.

This object is achieved by catalysts according to claim 1 which are characterized in particular by a ratio of the peak heights of the infrared absorption bands $v=3610\pm20$ cm$^{-1}$/$v=3680\pm20$ cm$^{-1}$ of greater than 1.8.

The present inventors surprisingly found that specifically catalysts with a specific ratio of the peak heights of the infrared absorption bands $v=3610\pm20$ cm$^{-1}$/$v=3680\pm20$ cm$^{-1}$ of greater than 1.8 and retaining the further features named in claim 1 result in improved selectivities and activities in specific catalytic processes.

The present invention makes it possible to provide tailor-made catalysts which facilitate a selective production of desired products in specific reactions. As already described, the use of catalysts based on aluminosilicate zeolites in processes for producing low olefins from oxygenates, preferably from methanol and/or dimethyl ether, or in processes for oligomerizing olefins, was already known. It was also already known from the state of the art that the structure of the zeolite used can have a significant influence on the activity and selectivity of the catalyzed reaction. One aspect which had not been sufficiently investigated in the state of the art is the question of which properties a 'finished' catalyst comprising a crystalline aluminosilicate zeolite and a binder matrix must have in order to give a desired improved selectivity and activity in specific reactions. Investigations had shown that the selectivity and activity of pure aluminosilicate zeolite cannot simply be extrapolated onto binder-containing catalysts based on aluminosilicate zeolite, as there is a complex interplay of physical and chemical interactions between the aluminosilicate zeolite and the binder. The strength of acid centres, their distribution as well as the concentration of aluminium inside the framework vary depending on the type, quantity and type of production of the aluminosilicate zeolite and binder used.

The present inventors surprisingly found that, despite the complex relationships described above, it is possible to characterize a catalyst by means of a parameter, namely the ratio of the peak heights of the infrared absorption bands $v=3610\pm20$ cm$^{-1}$/$v=3680\pm20$ cm$^{-1}$, which has particularly good catalytic properties. Namely it was found that catalysts with a ratio of the peak heights of the infrared absorption bands $v=3610\pm20$ cm$^{-1}$/$v=3680\pm20$ cm$^{-1}$ of greater than 1.8 are characterized by an improved selectivity in a process for producing low olefins from oxygenates as well as in a process for oligomerizing olefins. Within the framework of the present invention, infrared spectroscopy makes it possible to use the ratio of the peak heights of defined IR absorption bands to identify the particular properties of the various acid OH groups in the zeolite, at the binder and in the binder-zeolite boundary. The ratio of the peak heights of the infrared absorption bands $v=3610\pm20$ cm$^{-1}$/$v=3680\pm20$ cm$^{-1}$ is preferably 2 or greater, still more preferably 2.05 to 4.00 and particularly preferably 2.1 to 3.0.

The catalyst according to the invention has a SiO$_2$/Al$_2$O$_3$ weight ratio of from 2 to 9, preferably 2 to 7 and particularly preferably from 3 to 6. This is to be understood to mean that the catalyst has an elementary composition of SiO$_2$ and Al$_2$O$_3$ in a weight ratio of from 2:1 to 9:1, wherein naturally the catalyst can also contain further substances in addition to SiO$_2$ and Al$_2$O$_3$, such as for example magnesium oxide as possible binder component, as listed below.

The catalyst according to the invention comprises a crystalline aluminosilicate zeolite. Suitable zeolite materials include zeolites with TON structure (e.g. ZSM-22, IS1-1, KZ-2), MTT structure (e.g. ZSM-23, KZ-1), MFI structure (e.g. ZSM-5), MEL structure (e.g. ZSM-11), MTW structure (e.g. ZSM-12), zeolites with EUO structure or also ZSM-21, ZSM-35, ZSM-38, ZSM-4, ZSM-18 or ZSM-57. Mixtures of zeolites of varying structure can also be used. A pentasil-type zeolite is preferably involved, particularly preferably the zeolite has an MFI structure, in particular of ZSM-5 type. The zeolites are preferably present in the H form, i.e. the protonated form.

The catalyst according to the invention with a SiO$_2$/Al$_2$O$_3$ weight ratio of from 2 to 9 also contains a binder component, in addition to the zeolite component. The binder component is present in the catalyst in the form of a matrix in which the crystalline aluminosilicate zeolites are embedded. Inorganic oxides, preferably aluminium oxide, magnesium oxide, titanium oxide, zinc oxide, niobium oxide, zirconium oxide or silicon oxide, as well as mixtures thereof, in particular mixtures of the above-named oxides with aluminium oxide, as well as amorphous aluminosilicates and non-oxidic binders such as for example aluminium phosphates can be used as binders. Aluminium oxide is preferably used. Modified aluminium oxide such as for example phosphorous-modified aluminium oxide can likewise be used. The use of finely divided aluminium oxide binder, which is preferably obtained by hydrolysis of aluminium trialkylene or aluminium alcoholates or is used in the form of peptizable hydrous aluminium oxide, is particularly preferred. Peptizable hydrous aluminium oxide is quite particularly preferably used as binder. Further preferably, at least 95% of the particles of the peptizable hydrous aluminium oxide (relative to the average diameter) are ≤100 μm.

It is further preferred to use the binder in a quantity of from 5 to 60 wt.-%, even more preferably 10 to 40 wt.-%, particularly preferably 15 to 35 wt.-%, relative to the total weight of the catalyst (i.e. aluminosilicate and binder).

The BET surface area of the catalyst according to the invention is 250 to 500 m$^2$/g, preferably 300 to 450 m$^2$/g and particularly preferably 320 to 400 m$^2$/g, determined in accordance with DIN 66131.

Furthermore, the catalyst according to the invention is characterized by a low Na content of less than 200 ppm, preferably less than 150 ppm. The Na content is preferably less than 120 ppm, quite particularly preferably 20 to 110 ppm, still more preferably between 40 and 80 ppm.

The pore volume of the catalyst according to the invention, determined using the mercury porosimetry method in accordance with DIN 66133, is preferably 0.3 to 0.8 cm$^3$/g.

The production of a catalyst according to the invention can be carried out according to the following process, comprising the following steps:

(a) crystallizing an aluminosilicate from an aqueous suspension, containing a silicon source, an aluminium source, an alkali source and a template, (b) separating the aluminosilicate out of the suspension, followed by a drying step and a calcining step to remove the template from the aluminosilicate;

(c) exchanging the alkali ions contained in the aluminosilicate in aqueous medium with a proton-containing substance or a substance that yields protons when heated, wherein the molar ratio of the protons of the proton-containing or proton-yielding substance to aluminium in the aluminosilicate is from 5:1 to 50:1, followed by an optional washing with water, until the conductivity of the medium is less than 200 μS/cm, a drying and an optional intermediate calcining;

(d) mixing the ion-exchanged aluminosilicate from stage (c) with a binder;

(e) shaping the product from stage (d); and (f) final calcining of the product from stage (e).

During the production of the catalyst according to the invention, it is particularly important in order to achieve the particularly advantageous catalytic property that, to convert from the alkali form, in particular the Na form, to the H form with a proton-containing or proton-yielding acid, the molar ratio of the protons per aluminium atom present is in a range of from 5:1 to 50:1, before the zeolite is mixed with a binder and the obtained mixture is subjected to a shaping. Here, the inventive aspect is that the interaction between the zeolite treated under special conditions during the ion exchange and a binder results in a particular stabilizing of the aluminium atoms of the zeolite framework, which results in a ratio of the peak heights of the infrared absorption bands $v=3610\pm20$ $cm^{-1}/v=3680\pm20$ $cm^{-1}$ of greater than 1.8.

At the end of the process, the obtained product is subjected to a final calcining, wherein here it was surprisingly found that the thus-produced zeolite-binder mixture, i.e. the catalyst, has quite particularly advantageous catalytic properties if the final calcining is carried out at relatively low temperatures in the range of from 470 to 650° C. for up to 5 hours.

The aluminosilicate component is preferably produced according to the following process:

(a) in an aqueous reaction mixture containing a silicon source, an aluminium source, an alkali source and a template, an alkali aluminosilicate gel is produced in a manner known per se at increased temperature and optionally at increased pressure, and converted to a crystalline aluminosilicate, wherein however the reaction is terminated when the obtained primary crystallites have an average diameter of at least 0.01 μm, but less than 0.1 μm, preferably from 0.01 to 0.06 μm, in particular from 0.015 to 0.05 μm;

(b) the primary crystallites are separated out of the aqueous reaction medium as pre-agglomerates, dried and subjected to an intermediate calcining;

(c) to exchange the alkali ions in aqueous medium, the product from stage (b) is reacted with a proton-containing substance or a substance that yields protons when heated, wherein the molar ratio of the protons of the proton-containing or proton-yielding substance to aluminium in the aluminosilicate is from 5:1 to 50:1, preferably 10:1 to 45:1, particularly preferably from 15:1 to 40:1, quite particularly preferably from 20:1 to 36:1, then the obtained product is separated off, optionally washed with water until the conductivity of the medium is less than 200 μS/cm, preferably less than 100 μS/cm, dried, and optionally subjected again to an intermediate calcining, whereupon an agglomerate fraction of from approx. 5 to 500 μm is separated off;

(d) the agglomerate fraction of stage (c) is mixed with the finely divided hydrous aluminium oxide;

(e) the product from stage (d) is subjected to a shaping; and (f) the product from stage (e) is subjected to a final calcining.

The importance of the individual stages by which the catalyst according to the invention can be obtained is explained in further detail below:

In stage (a) firstly an aqueous reaction mixture containing a silicon source (for example colloidal silicic acid or an alkali silicate), an alkali and an aluminium source (alkali aluminate, in particular sodium aluminate) and a template, is produced.

Within the framework of the present invention, a substance can perform several functions; for example a substance can serve as alkali source and as aluminium source, or as silicon source and as alkali source, or also as alkali source, aluminium source and silicon source. It was found that particularly advantageous catalysts can be produced using an alkali aluminate, in particular sodium aluminate, as alkali and aluminium source. In stage a) (primary synthesis of the crystalline aluminosilicate), there is no (separate) addition of acid. In particular, compared with other known processes, no mineral acids such as sulphuric acid are used in the reaction mixture during the primary synthesis. In the process, the problems arising when handling (strong) acids are avoided and advantageous catalysts are obtained.

If the catalyst according to a particularly preferred embodiment according to the invention is to be used in a process for converting methanol to propylene, in particular a process according to DE 100 27 159 A1, the disclosure therein regarding same being hereby incorporated into the description, the percentages by weight between silicon source and aluminium source are chosen in particular such that crystalline aluminosilicates with a Si/Al atomic ratio between approximately 50 and 250, preferably approximately 50 and 150, in particular approximately 75 to 120, still more preferably 85 to 110, are obtained. If the finished catalyst according to a further particularly preferred embodiment according to the invention is provided for use in a process for oligomerizing, the percentages by weight between silicon source and aluminium source are chosen in particular such that crystalline aluminosilicates with a Si/Al atomic ratio between approximately 10 and 100, preferably between approximately 20 and 65, in particular approximately 25 to 55, still more preferably 30 to 50, are obtained.

An alkali aluminosilicate gel is produced in a manner known per se from the reaction mixture at increased temperature and optionally at increased pressure. It is already possible to operate at temperatures starting from 90° C., but the reaction times in this case are comparatively long (approximately 1 week). Therefore temperatures of from 90 to 190° C., in particular from 90 to 150° C. are preferably used, wherein at temperatures of more than 100° C. (under normal conditions) excess pressure is automatically established depending on the temperature. The aluminosilicate gel is converted to a crystalline aluminosilicate in the course of the reaction. If the temperature of the reaction mixture is higher than 190° C., the growth of the aluminosilicate primary crystallites is too rapid and primary crystallites that are too large are readily obtained, while simultaneously aluminosilicate gel is still present in the reaction mixture.

Tetraalkylammonium compounds, preferably tetrapropylammonium hydroxide (TPAOH) or tetrapropylammonium bromide (TPABr) are used as templates. Mixtures of ammonia or an organic amine and a further organic compound from the group of alcohols, preferably butanol, can also be used as templates. The aqueous reaction mixture from stage (a) preferably has a pH of from 10 to 13. At a pH of less than 10, the conversion of the aluminosilicate gel to the crystalline aluminosilicate proceeds comparatively slowly. At pH values higher than 13, the aluminosilicate crystals can in some cases dissolve again. The formation of the crystalline aluminosilicate primary crystallites can be controlled by suitable selection of the silicon source, the aluminium source, the alkali source and the template as well as by suitable selection of the temperature and of the pH and stirring speed. When carrying out the synthesis, the reaction can be terminated when the obtained primary crystallites have an average diameter of at least 0.01 μm and less than 0.1 μm, preferably in the range of from 0.01 to 0.06 µm, in particular from 0.015 to 0.05 µm. To this end, several test runs are carried out. After only a few tests, the optimum parameters on the basis of which the required size ranges of the primary crystallites are reached can be ascertained. A further sign of the end of the reaction is that the pH of the reaction mixture suddenly increases. It is not necessary for a new reaction mixture to be produced in each case. Instead, to produce the aluminosilicate gel, the silicon source, the alkali source, the aluminium source, the template and the water from the mother liquors of previous syntheses can be used and supplemented by the quantities of the named compounds required for the synthesis of the aluminosilicate gel. The measurement of the average diameter of the primary crystallites is carried out as described in EP 1 424 128 A1, the disclosure of which is incorporated into the present application.

The formation of the aluminosilicate primary crystallites from stage (a) preferably takes place at a pH between 10 and 13, wherein the reaction mixture is stirred. In this way, the size distribution of the primary crystallites is homogenized. However, the stirring speed is preferably to be no more than 900 rpm. At higher stirring speeds, the proportion of smaller primary crystallites is higher, which is advantageous provided that it is ensured that the average diameter of all the primary crystallites is at least 0.01 µm.

In stage (b), the primary crystallites are separated out of the aqueous reaction medium as pre-agglomerates, i.e. not as individual crystallites. This is preferably achieved by adding a flocculant to the aqueous reaction medium. In general, a cationic organic macromolecular compound is used as flocculant. The flocculant not only facilitates the separation off of the primary crystallites from the reaction medium (improved filterability), but also causes the primary crystallites to combine to form pre-agglomerates which are already largely equivalent in terms of size, structure and accumulation of the primary crystallites to the agglomerates formed in the subsequent stage. The pre-agglomerates are dried and subjected to an intermediate calcining, which is first preferably carried out in an inert atmosphere at approximately 200 to 350° C., in particular at approximately 250° C., wherein one part of the template or its decomposition product is desorbed. The intermediate calcining can then be completed in an oxidizing atmosphere at approximately 500 to 600° C., wherein any residual quantity of template still present is burnt off. In general, the pre-agglomerates are subjected to intermediate calcining for approximately 1 to 20 hours in the inert atmosphere and approximately 1 to 30 hours in the oxidizing atmosphere.

In stage (c), to exchange the alkali ions in aqueous medium, the product from stage (b) is reacted with a proton-containing substance or a substance that yields protons when heated. For example, the ion exchange can be carried out with the help of a diluted mineral acid (e.g. hydrochloric acid or sulphuric acid) or an organic acid (e.g. acetic acid). The molar ratio of the protons of the proton-containing or proton-yielding substance to aluminium is in the range of from 5:1 to 50:1, preferably 10:1 to 45:1, particularly preferably from 15:1 to 40:1, quite particularly preferably 20:1 to 36:1. A ratio of the peak heights of the infrared absorption bands $v=3610\pm20$ $cm^{-1}/v=3680\pm20$ $cm^{-1}$ of greater than 1.8 is thereby obtained. The ion exchange is preferably carried out accompanied by stirring for at least an hour at temperatures between 25 and 100° C., wherein at least some of the alkali ions in the pre-agglomerates of the primary crystallites are exchanged for hydrogen ions. If necessary, the ion exchange can be repeated under the same conditions. After the exchange of the alkali ions in aqueous medium, the proton-containing product (H zeolite) is separated off (for example by filtration), dried and optionally subjected again to an intermediate calcining. After the separation (e.g. filtration or sedimentation) and before the drying, the ion-exchanged product is preferably washed with water (distilled water) until the conductivity of the medium (wash water after use) is less than 200, preferably less than 100 µS/cm. It was namely surprisingly found that under such washing conditions catalysts according to the invention result which have a very low Na content of less than 200 ppm, preferably less than 150 ppm, still more preferably less than 120 ppm, quite particularly preferably 20 to 110 ppm, still more preferably between 40 and 80 ppm, and which are characterized by a ratio of the peak heights of the infrared absorption bands $v=3610\pm20$ $cm^{-1}/v=3680\pm20$ $cm^{-1}$ of greater than 1.8.

The intermediate calcining is carried out at temperatures of from 400 to 800° C., preferably at temperatures of from 450 to 600° C. over a period of from 2 to 20 hours.

The product obtained after the intermediate calcining contains agglomerates which are ≥500 µm on the one hand, and dust portions which are ≤5 µm on the other. An agglomerate fraction of approximately 5 to 500 µm is therefore separated off.

In stage (d), this agglomerate fraction is mixed with the finely divided hydrous aluminium oxide. The hydrous aluminium oxide is preferably characterized here by particles 95 or more of which have a diameter of less than 100 µm.

This value, averaged over a plurality of crystallites, is relative to the average diameter which is defined as the average diameter of the primary crystallites.

The hydrous aluminium oxide is substantially responsible for setting the pore volume of the catalyst. The quantity of the finely divided hydrous aluminium oxide binder is preferably approximately 10 to 40 wt.-%, relative to the total weight of the product (the mixture) of stage (d). The finely divided hydrous aluminium oxide binder is preferably peptizable aluminium oxide, which is particularly poor in Na and Fe. To peptize the hydrous aluminium oxide, an acid concentration of from 0.15 to 2.5 mol $H^+$/mol $Al_2O_3$, preferably from 0.20 to 1.5 mol $H^+$/mol $Al_2O_3$ and in particular from 0.4 to 1.0 mol $H^+$/mol $Al_2O_3$ is preferably used. The peptizing can be carried out in principle with organic or inorganic acids in a concentration range of the acid of from 0.1% to 100%. For example, organic acids such as 100% acetic acid or diluted inorganic acids such as 52% nitric acid etc. can be used.

In stage (e), the product from stage (d) is subjected to a shaping. The ratio of the peak heights of the infrared absorption bands $v=3610\pm20$ $cm^{-1}/v=3680\pm20$ $cm^{-1}$ is greater than 1.8 in the obtained product. By shaping is usually meant the transformation of a material into shaped bodies of precisely defined dimensions. These include extrudates, spherical or honeycomb bodies, pellets, granules and other shaped bodies. In particular, the shaping can start from a plasticizable mass which, after the shaping has finished, is subjected to a final calcining (see stage f) in order to achieve the desired stability.

The product from stage (e) is subjected to a final calcining. In general, this can be carried out for 1 to 12 hours at temperatures of between approximately 460° C. and 850° C. Advantageously, the final calcining can be carried out at a temperature of from 470 to 650° C. for up to 5 hours, in particular at a temperature of from 480 to 600° C. for 1 to 5 hours, preferably 1 to 4 hours.

Further preferably, a catalyst according to the invention can be produced based on the above-described process, wherein in stage (a) the reaction is terminated when the obtained primary crystallites have an average diameter of at least 0.1 µm and less than 0.9 µm.

As mentioned above, the thus-obtained end product can be particularly advantageously used in processes for producing olefins by converting oxygenates or in processes for oligomerizing olefins.

However, in principle a use in other carbon conversion reactions, such as in particular dewaxing processes, alkylations, the conversion of paraffin to aromatic compounds (CPA) as well as related reactions is also possible.

Part of the invention is therefore a process for producing olefins from oxygenates, preferably methanol, dimethyl ether or mixtures thereof, wherein an educt gas, i.e. the gaseous starting material, is passed over the catalyst according to the invention. By oxygenates is meant within the framework of the present invention oxygen compounds, in particular organic oxygen compounds such as alcohols and ethers. The present invention therefore preferably relates to a process for producing low olefins from oxygen compounds (oxygenates to olefins), preferably alcohols, particularly preferably methanol (methanol to olefins, MTO) by reacting for example a reaction mixture containing methanol and/or dimethyl ether steam and steam in a reactor using an indirectly cooled catalyst according to the invention. In particular the yield of propylene per cycle is increased with the process according to the invention.

The reaction with the catalyst according to the invention is carried out particularly preferably (a) at a total pressure of from 10 to 150 kPa, preferably at a total pressure of from 50 to 140 kPa, (b) at a weight ratio between water and methanol or methanol equivalents of from 0.1 to 4.0, preferably from 0.5 to 3, and (c) at a temperature of the reactor cooling medium of from 280 to 570° C., preferably from 400 to 550° C. Such a preferred process is described in EP 0 448 000 A1, the disclosure of which regarding same is hereby incorporated into the description. Further preferred processes are described in EP 1289912 B1 and DE 102006026103 A1, the disclosure of which regarding same is hereby incorporated into the description.

Part of the invention is furthermore a process for oligomerizing olefins, wherein an educt gas is conducted over the catalyst according to the invention. The educt gas, i.e. gaseous olefin feed, can also contain alkanes in addition to alkenes. The olefin feed preferably contains propene, butene (1-butene, 2-butene, isobutene) or mixtures thereof, optionally also further alkenes such as octene or alkanes such as propane. The olefin feed can also contain hydrogen or nitrogen in a range of from 0.1 to 50 wt.-%. The substance ratio of propene to butene in the mixtures, which can optionally also contain further components as described above, is preferably 60:40 to 40:60. It is furthermore preferred if the olefin feed contains smaller quantities of water in the range of from 0.05 to 0.25 mol.-%, relative to the hydrocarbon portion in the feed. In particular the yield of diesel fraction per cycle is increased with the process according to the invention. By diesel fraction is meant within the framework of the present invention a mixture of long-chained olefins, aliphatics and cyclic compounds.

The reaction with the catalyst according to the invention is particularly preferably carried out (a) with an olefin feed of from 0.5 to 2.0 kg/kg/h with the composition of propene to 1-butene in the weight ratio of 60:40 to 40:60 and a gasoline dilution in the boiling-point range of from 45° C. to 170° C., (b) at a total pressure of from 1 to 100 bar (100-10000 kPa), preferably 30 to 75 bar (3000-7500 kPa), particularly preferably 35 to 60 bar (3500-6000 kPa), and (c) at a temperature of the reactor of from 180 to 400° C., preferably 220 to 320° C.

The use of the catalysts according to the invention in the previously named processes is likewise a subject of the invention. Reference is made to the above statements in respect of preferred embodiments.

SHORT DESCRIPTION OF THE FIGURES

Figure 1:
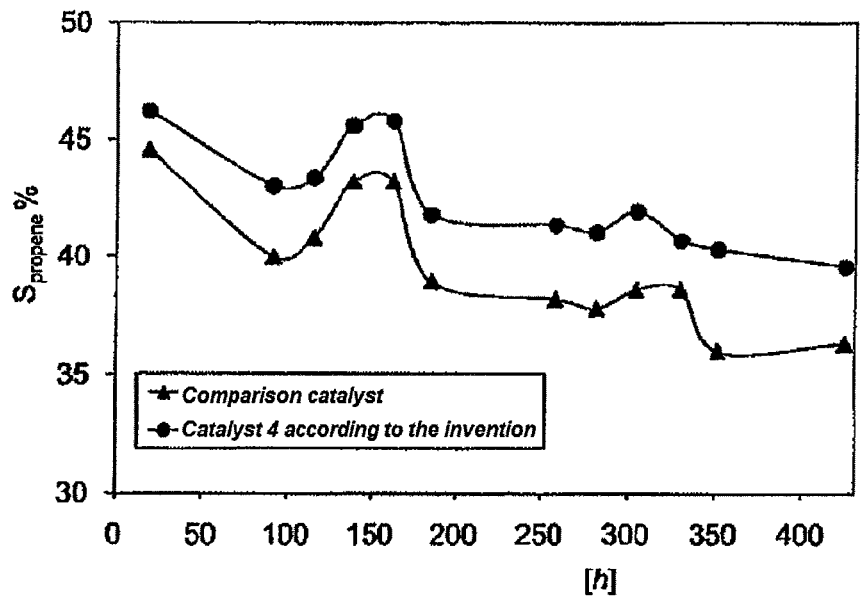
FIG. 1 shows the propene selectivity as a function of the reaction duration in application example 1.

The present invention is explained by the examples below.
Description of the IR Measurements of the Catalysts For the measurements, the samples to be measured were tabletted and then activated in vacuum (approx. $10^{-6}$ mbar) at 450° C. for 1 h. The measuring was carried out after cooling to room temperature in the sample chamber. The single-beam IR measurements were taken with a Perkin Elmer 2000 spectrometer. The representation of the spectra was converted by means of computer software from a plotting of the signal intensities to a plotting of the absorption; for quantitative determination of the peak heights a base line correction was also carried out. The spectra were recorded in the range of from 4000 to 800 $cm^{-1}$ at a resolution of 2 $cm^{-1}$. By means of the intensity of the peak heights of the absorption band, the number of species present in the corresponding sample which can be allocated to this band can be calculated. To compare several samples with one another, the intensities are standardized to an internal standard. The standardization is carried out in relation to the skeletal vibration of the aluminosilicate zeolite. To assess the relative quantities of the individual acid groups, the peak height of the band at 3610±20 $cm^{-1}$ was compared with the peak height of the band at 3680±20 $cm^{-1}$ (intensity ratio (3610±20 $cm^{-1}$/3680±20 $cm^{-1}$).

Measurement Methods

The conductivity can be measured with a standard conductivity measurement device, for example a WTW 340i pH/conductometer with conductivity measuring cell TetraCon 325. The measurement is carried out as standard at room temperature.

Production of Catalyst 1 According to the Invention

The aluminosilicate which was used to produce catalyst 1 was obtained according to the following procedure: the synthesis was carried out by blending two part-suspensions A and B. Suspension A was obtained by dissolving 69 kg tetrapropylammonium bromide salt in 675 l dist. $H_2O$ and then adding 155 kg silicic acid. Solution B was produced by incorporating and dissolving 19 kg NaOH as well as then 8.35 kg sodium aluminate in a total of 43 l dist. $H_2O$. The solution was then blended with solution A accompanied by intimate stirring, re-rinsed with 10 l dist. $H_2O$, further stirred for approx. 30 min and then heated to a reaction temperature of 130° C. in a pressure-tight synthesis chamber. The reaction suspension was stirred constantly at this temperature for 107 h, then cooled and the solid formed separated from the mother liquor by filtration. The thus-obtained filter cake was again suspended in dist. $H_2O$ in order to separate off excess foreign ions. The zeolitic material was sedimented by means of cationic flocculant, the excess solution pumped off and this washing process repeated several times. The filter cake was then pre-dried to remove most of the adhering water and then calcined to remove the organic template. For this, the filter cake was first heated under nitrogen at a heating rate of 60° C./h to a temperature of 350° C. and stored at this temperature for 16 h. This was followed by heating under air atmosphere at a heating rate of 60° C./h to 540° C. and this temperature maintained for 24 hours.

To convert the Na form into the catalytically active H form, 375 l of an aqueous hydrochloric acid solution was added to 75 kg of the Na form, wherein the acid concentration was selected such that the atomic ratio $H^+$ of the hydrochloric acid solution to aluminium in the aluminosilicate was approx. 7:1. It was shown here that the effective acid activity was small enough to minimize the dissolution of aluminium atoms out of the aluminosilicate framework, which has a positive influence in particular on the catalytic properties of the material during the oligomerizing of olefins. For the ion exchange, the acid was heated to 80° C. and the aluminosilicate then added. The suspension was stirred for a further hour and the finely divided solid taken to sedimentation by the addition of a cationic flocculant. The remaining solution was decanted and the ion exchange described above carried out yet again by adding a further 375 l of the hydrochloric acid solution described above. After the second ion exchange was finished, after fresh addition of the cationic flocculant the solid was separated off by filtration. The filter cake was then washed in order to remove foreign ions. The washings were terminated when the used wash water displayed a conductivity of approx. 50 µS/cm. The filter cake was reduced to a particle size of less than 2 mm with a granulator customary in the trade and then heated in a calcination oven at a heating rate of 60° C./h to a final temperature of 540° C. and stored at this temperature for 10 hours.

For the shaping, the H-form powder was first ground by means of a laboratory mill to a particle size of less than 100 µm and 400 g provided for the subsequent shaping. 200 g hydrous aluminium oxide, which was used as binder, was stirred with 204 ml dist. $H_2O$ to form a low-viscosity mass. In the next step, 248 g of a nitric acid solution (31 wt.-% $HNO_3$) was slowly added dropwise, as a result of which a peptizing of the hydrous aluminium oxide set in. This highly viscous paste was kneaded in a kneader with the aluminosilicate material until it was completely plasticized, 34 g steatite oil was then also incorporated. The shaping was carried out with an extruder customary in the trade; shaped bodies with a diameter of approx. 3 mm and a length of approx. 6 mm were obtained. A final calcining was carried out at 600° C. for 5 hours.

The obtained catalyst has a $SiO_2/Al_2O_3$ weight ratio of 4.0, a BET surface area of 404 m²/g, and a Na content of 43 ppm. The ratio of the peak heights of the IR absorption bands at 3610±20 cm$^{-1}$ and 3680±20 cm$^{-1}$ is shown in Table 1.

Production of Catalyst 2 According to the Invention

The aluminosilicate which was used to produce catalyst 2 was obtained according to the following procedure: the synthesis was carried out by blending two part-suspensions A and B. Suspension A was obtained by incorporating 960 kg tetrapropylammonium bromide salt and 4487 kg silicic acid into 15550 kg dist. water. Solution B was produced by dissolving 126 kg sodium aluminate in 1200 kg caustic soda solution (8.3 wt.-%). The solution was blended with solution A accompanied by intimate stirring, a further 190 kg of a 50% caustic soda solution was added, the reaction mixture was re-rinsed with 450 l water and heated to a reaction temperature of 130° C. in a pressure-tight synthesis chamber. The reaction suspension was stirred constantly at this temperature for 60 h, then cooled and the solid formed separated from the mother liquor by filtration and adhering foreign ions removed with wash water. The filter cake was then pre-dried to remove most of the adhering water and then calcined to remove the organic template. For this, the filter cake was first heated under nitrogen at a heating rate of 230° C./h to a temperature of 250° C. and carefully further heated within 12 h to a temperature of 540° C. The zeolite was then stored under air atmosphere at this temperature for a further 6 hours.

To convert the Na form into the catalytically active H form, 5410 l of an aqueous hydrochloric acid solution was added to 1100 kg of the Na form, wherein the acid concentration was selected such that the atomic ratio $H^+$ of the hydrochloric acid solution to aluminium in the aluminosilicate was approx. 15:1. It was shown here that the effective acid activity was small enough to minimize the dissolution of aluminium atoms out of the aluminosilicate framework, which has a positive influence in particular on the catalytic properties of the material during the conversion of olefins to diesel. For the ion exchange, the acid was heated to 80° C. and the aluminosilicate then added. The suspension was stirred for two further hours and the finely divided solid taken to sedimentation by the addition of a cationic flocculant. The remaining solution was decanted and the ion exchange described above carried out yet again by adding a further 5410 l of the hydrochloric acid solution described above. After the second ion exchange was finished, after fresh addition of the cationic flocculant the solid was separated off by filtration. The filter cake was then washed in order to remove foreign ions. The filter cake was then heated in a calcination oven under air atmosphere within 8.5 h to a final temperature of 540° C. and stored for 2.5 hours at this temperature.

For the shaping, the H-form powder was first ground by means of a laboratory mill to a particle size of less than 150 µm and 400 g provided for the subsequent shaping. 199 g hydrous aluminium oxide, which was used as binder, was stirred with 204 ml dist. $H_2O$ to form a low-viscosity mass. In the next step, 248 g of a nitric acid solution (31 wt.-% $HNO_3$) was slowly added dropwise, as a result of which a peptizing of the hydrous aluminium oxide set in. This highly viscous paste was kneaded in a kneader with the aluminosilicate material until it was completely plasticized, 34 g steatite oil was then also incorporated. The shaping was carried out with an extruder customary in the trade; shaped bodies with a diameter of approx. 3 mm and a length of approx. 6 mm were obtained. A final calcining was carried out at 600° C. for 5 hours.

The obtained catalyst has a $SiO_2/Al_2O_3$ weight ratio of 4.4, a BET surface area of 386 m²/g, and a Na content of 62 ppm. The ratio of the peak heights of the IR absorption bands at 3610±20 cm$^{-1}$ and 3680±20 cm$^{-1}$ is shown in Table 1.

Production of Catalyst 3 According to the Invention

The aluminosilicate which was used to produce catalyst 3 was obtained according to the following procedure: the synthesis was carried out by blending two part-suspensions A and B. Suspension A was obtained by dissolving 95.7 kg tetrapropylammonium bromide salt in 600 L dist. $H_2O$ and then adding 215.8 kg silicic acid, then 30 l dist. $H_2O$ was added for re-rinsing. Solution B was produced by incorporating and dissolving 33.1 kg NaOH as well as then 2.0 kg sodium aluminate in a total of 50 l dist. $H_2O$. The solution was then blended with solution A accompanied by intimate stirring and, after re-rinsing with 22 l, heated to a reaction temperature of 130° C. in a pressure-tight synthesis chamber. The reaction suspension was stirred constantly at this temperature for 60 h, then cooled and the solid formed separated from the mother liquor by decanting and washed with wash water in order to remove foreign ions. The filter cake was then predried to remove most of the adhering water and then calcined to remove the organic template. For this, the filter cake was first heated under nitrogen at a heating rate of 60° C./h to a temperature of 350° C. and stored for 15 h at this temperature.

This was followed by heating under air atmosphere at a heating rate of 60° C./h to 540° C. and this temperature maintained for 24 hours.

To convert the Na form into the catalytically active H form, 346 l of an aqueous hydrochloric acid solution was added to 70.3 kg of the Na form, wherein the acid concentration was selected such that the atomic ratio $H^+$ of the hydrochloric acid solution to aluminium in the aluminosilicate was approx. 28:1. It was shown here that the effective acid activity was small enough to minimize the dissolution of aluminium atoms out of the aluminosilicate framework, which has a positive influence in particular on the catalytic properties of the material during the conversion of methanol to olefins. For the ion exchange, the acid was heated to 80° C. and the aluminosilicate then added. The suspension was stirred for a further hour and the finely divided solid taken to sedimentation by the addition of a cationic flocculant. The remaining solution was decanted and the ion exchange described above carried out yet again by adding a further 346 l of the hydrochloric acid solution described above. After the second ion exchange was finished, flocculant was added again and the remaining solution removed by decanting. The filter cake was then washed by means of a sedimentation wash in order to remove foreign ions. The washings were terminated when the used wash water displayed a conductivity of approx. 80 μS/cm. After this step the zeolite suspension was introduced into a filter press in order to achieve a separation of the aqueous phase. The moist filter cake was then dried, reduced to a particle size of less than 2 mm with a granulator customary in the trade and then heated in a calcination oven under air atmosphere at a heating rate of 60° C./h to a final temperature of 540° C. and stored at this temperature for 10 hours.

For the shaping, the H-form powder was first ground by means of a laboratory mill to a particle size of less than 100 μm and 3000 g provided for the subsequent shaping. 889 g hydrous aluminium oxide, which was used as binder, was stirred with 900 ml dist. $H_2O$ to form a low-viscosity mass. In the next step, 1108 g of a nitric acid solution (31 wt.-% $HNO_3$) was slowly added dropwise, as a result of which a peptizing of the hydrous aluminium oxide set in. This highly viscous paste was kneaded in a kneader with the aluminosilicate material until it was completely plasticized, 252 g steatite oil was then also incorporated. The shaping was carried out with an extruder customary in the trade; shaped bodies with a diameter of approx. 3 mm and a length of approx. 6 mm were obtained. A final calcining was carried out at 600° C. for 5 hours.

The obtained catalyst has a $SiO_2/Al_2O_3$ weight ratio of 4.6, a BET surface area of 334 m²/g, and a Na content of 30 ppm. The ratio of the peak heights of the IR absorption bands at 3610±20 cm$^{-1}$ and 3680±20 cm$^{-1}$ is shown in Table 1.

Production of Catalyst 4 According to the Invention

The aluminosilicate which was used to produce catalyst 4 was obtained according to the following procedure: the synthesis was carried out by blending two part-suspensions A and B. Suspension A was obtained by dissolving 95.7 kg tetrapropylammonium bromide salt in 600 l dist. $H_2O$ and then adding 215.8 kg silicic acid, then 30 l dist. $H_2O$ was added for re-rinsing. Solution B was produced by incorporating and dissolving 33.1 kg NaOH as well as then 2.0 kg sodium aluminate in a total of 50 l dist. $H_2O$. The solution was blended with solution A accompanied by intimate stirring and, after re-rinsing with 22 l, heated to a reaction temperature of 130° C. in a pressure-tight synthesis chamber. The reaction suspension was stirred constantly at this temperature for 60 h, then cooled and the solid formed separated from the mother liquor by decanting, and washed with wash water in order to remove foreign ions. The filter cake was then pre-dried to remove most of the adhering water and then calcined to remove the organic template. For this, the filter cake was first heated under nitrogen at a heating rate of 60° C./h to a temperature of 350° C. and stored at this temperature for 15 h. This was followed by heating under air atmosphere at a heating rate of 60° C./h to 540° C. and this temperature maintained for 24 hours.

To convert the Na form into the catalytically active H form, 346 l of an aqueous hydrochloric acid solution was added to 70.3 kg of the Na form, wherein the acid concentration was selected such that the atomic ratio $H^+$ of the hydrochloric acid solution to aluminium in the aluminosilicate was approx. 28:1. It was shown here that the effective acid activity was small enough to minimize the dissolution of aluminium atoms from the aluminosilicate framework, which has a positive influence in particular on the catalytic properties of the material during the conversion of methanol to olefins. For the ion exchange, the acid was heated to 80° C. and the aluminosilicate then added. The suspension was stirred for a further hour and the finely divided solid taken to sedimentation by the addition of a cationic flocculant. The remaining solution was decanted and the ion exchange described above carried out yet again by adding 346 l of the hydrochloric acid solution described above. After the second ion exchange was finished, flocculant was added again and the remaining solution removed by decanting. The filter cake was then washed by means of a sedimentation wash in order to remove foreign ions. After this step the zeolite suspension was introduced into a filter press in order to achieve a separation of the aqueous phase. The moist filter cake was then dried, reduced to a particle size of less than 2 mm with a granulator customary in the trade and then heated in a calcination oven under air atmosphere at a heating rate of 60° C./h to a final temperature of 540° C. and stored at this temperature for 10 hours.

For the shaping, the H-form powder was first ground by means of a laboratory mill to a particle size of less than 100 μm and 750 g provided for the subsequent shaping. 220 g hydrous aluminium oxide, which was used as binder, was stirred with 500 ml of a nitric acid solution (17 wt.-% $HNO_3$), as a result of which a peptizing set in. This highly viscous paste was kneaded in a kneader with the aluminosilicate material until it was completely plasticized, 63 g steatite oil was then also incorporated. The shaping was carried out with an extruder customary in the trade; shaped bodies with a diameter of approx. 3 mm and a length of approx. 6 mm were obtained. A final calcining was carried out at 600° C. for 5 hours.

The obtained catalyst has a $SiO_2/Al_2O_3$ weight ratio of 4.6, a BET surface area of 333 m²/g, and a Na content of 47 ppm. The ratio of the peak heights of the IR absorption bands at 3610±20 cm$^{-1}$ and 3680±20 cm$^{-1}$ is shown in Table 1.

Preparation of the Comparison Catalyst

To produce the comparison catalyst, 10.6 kg sodium aluminate was first dissolved in 1400 kg of a caustic soda solution (6.9 wt.-%). Parallel thereto, a suspension of 4545 kg silicic acid and 1992 kg tetrapropylammonium bromide in 11639 kg dist. water was produced. Both mixtures were then combined accompanied by constant stirring, a further 1224 kg of a caustic soda solution (48 wt.-%) added, the reaction mixture was re-rinsed with 1190 kg dist. water and heated to a temperature of 130° C. in a pressure-tight reaction vessel and stirred constantly for 60 h. The reaction suspension was then cooled and the solid formed separated from the mother liquor by filtration and washed with wash water in order to remove foreign ions.

The filter cake was then pre-dried to remove most of the adhering water and then calcined to remove the organic template. For this, the filter cake was first heated under nitrogen at a heating rate of 230° C./h to a temperature of 250° C. and carefully further heated within 12 h to a temperature of 540° C. The zeolite was then stored under air atmosphere at this temperature for a further 6 hours.

To convert the Na form into the catalytically active H form, 6500 l of an aqueous hydrochloric acid solution was added to 1500 kg of the Na form, wherein the acid concentration was selected such that the atomic ratio $H^+$ of the hydrochloric acid solution to aluminium in the aluminosilicate was approx. 66:1. For the ion exchange, the acid was heated to 80° C. and the aluminosilicate then added. The suspension was stirred for two further hours and the finely divided solid taken to sedimentation by the addition of a cationic flocculant. The remaining solution was decanted and the ion exchange described above carried out yet again by adding a further 5490 l of the hydrochloric acid solution described above. After the second ion exchange was finished, after fresh addition of the cationic flocculant the solid was separated off by filtration. The filter cake was then washed in order to remove foreign ions. The filter cake was then heated in a calcination oven under air atmosphere within 8.5 h to a final temperature of 540° C. and stored for 2.5 hours at this temperature.

For the shaping, the H-form powder was first ground by means of a laboratory mill to a particle size of less than 100 µm and 3000 g provided for the subsequent shaping. 1838 g hydrous aluminium oxide, which was used as binder, was stirred with 1880 ml dist. $H_2O$ to form a low-viscosity mass. In the next step, 2290 g of a nitric acid solution (31 wt.-% $HNO_3$) was slowly added dropwise, as a result of which a peptizing of the hydrous aluminium oxide set in. This highly viscous paste was kneaded in a kneader with the aluminosilicate material until it was completely plasticized, 252 g steatite oil was then also incorporated. The shaping was carried out with an extruder customary in the trade; shaped bodies with a diameter of approx. 3 mm and a length of approx. 6 mm were obtained. A final calcining was carried out at 600° C. for 5 hours.

The obtained catalyst has a $SiO_2/Al_2O_3$ weight ratio of 4.1, a BET surface area of 291 m²/g, and a Na content of 26 ppm. The ratio of the peak heights of the IR absorption bands at $3610\pm20$ cm$^{-1}$ and $3680\pm20$ cm$^{-1}$ is shown in Table 1.

TABLE 1

Ratios of the peak heights (intensity) of the IR absorption bands

| Catalyst | Peak height $3680 \pm 20$ cm$^{-1}$ | Peak height $3610 \pm 20$ cm$^{-1}$ | Ratio of peak heights $3610 \pm 20$ cm$^{-1}$/ $3680 \pm 20$ cm$^{-1}$ |
|---|---|---|---|
| Catalyst 1 | 0.00179 | 0.00394 | 2.20 |
| Catalyst 2 | 0.00140 | 0.00285 | 2.04 |
| Catalyst 3 | 0.00071 | 0.00208 | 2.93 |
| Catalyst 4* | 0.0622 | 0.1815 | 2.92 |
| Comparison cat. | 0.00090 | 0.00130 | 1.44 |

*Measurement with IR spectrometer Thermo Nicolet 4700 with MCT detector

APPLICATION EXAMPLE 1

A test for converting methanol to olefin can be carried out by conducting educt gas, in particular a reaction mixture containing methanol and/or dimethyl ether steam and optionally steam, in a reactor over the catalyst according to the invention. The comparison catalyst described above can be used in a comparison test. The test can be carried out at temperatures in the region of from 400 to 550° C., preferably 430 to 500° C. The catalyst according to the invention is intended to result in an increased propylene yield.

The catalyst 4 according to the invention was used in a process for converting oxygenates to olefins. Used as the oxygenate was a reaction mixture containing methanol and/or dimethyl ether steam and optionally steam, which was conducted in a reactor over the catalyst according to the invention. For comparison, a catalyst was used which has a peak ratio outside the range claimed according to the invention, see Table 1.

The reaction of application example 1 was carried out as follows:

The catalyst 4 according to the invention and the comparison catalyst were filled into a vertical fixed-bed reactor and treated with steam for 48 h. The actual reaction was then started, wherein a reaction mixture consisting of methanol and steam was conducted over the catalyst. The loading of the catalysts with methanol was 1/h, i.e. 1 g methanol was conducted per hour over 1 gram catalyst. The temperature at the reactor inlet was 450° C., the test was carried out for 425 h.

The selectivities and methanol conversion rates of the catalyst 4 according to the invention as well as those of the comparison catalyst for different durations (tos) are given in Table 2:

TABLE 2

Propene selectivity as a function of duration

| tos [h] | Propene selectivity [%] | | Methanol conversion [%] | |
|---|---|---|---|---|
| | Catalyst 4 | Comparison catalyst | Catalyst 4 | Comparison catalyst |
| 91 | 43.0 | 40.0 | 98.6 | 94.0 |
| 139 | 45.6 | 43.2 | 97.8 | 93.1 |
| 186 | 41.8 | 38.9 | 97.2 | 91.5 |
| 305 | 41.9 | 38.6 | 95.7 | 90.5 |
| 352 | 40.3 | 36.0 | 94.9 | 89.5 |
| 424 | 39.5 | 36.3 | 94.5 | 89.0 |

Figure 2:
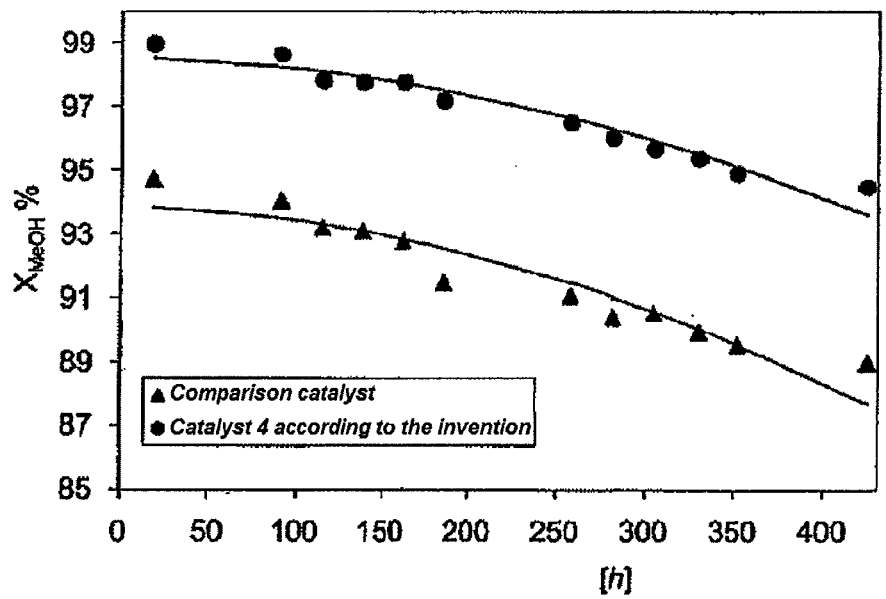
FIG. 2 shows the methanol conversion as a function of the reaction duration in application example 1.

The progress of the selectivities and methanol conversions is shown graphically in FIG. 1 and FIG. 2.

It is clearly evident that the catalyst according to the invention is superior both in terms of the propylene selectivity and the methanol conversion.

APPLICATION EXAMPLE 2

For the test for oligomerizing olefins, the performance of the catalyst according to the invention can be compared with the performance of the comparison catalyst. In the test, a propene/butene mixture (optionally with further components) can be reacted under oligomerizing conditions, wherein the catalyst according to the invention is intended to result in a comparatively high yield of products of the diesel fraction. The technical background is that, although an oligomerizing reaction is involved, further products also form in addition to olefins, with the result that ultimately a relatively complex mixture of long-chained olefins, aliphatics and cyclic compounds forms which is called diesel fraction. The detection can be carried out by a distillate separation of the diesel fraction from further product constituents (the more diesel can be detected by distillative separation, the better the selectivity of the catalyst). The test can be carried out in particular with an olefin feed which contains the following components: propene (preferably 8 wt.-%), propane (preferably 8 wt.-%), 1-butene (preferably 8 wt.-%), 1-octene (preferably 40 wt.-%) and nitrogen (preferably 36 wt.-%).

The invention claimed is:

1. Catalyst with a $SiO_2/Al_2O_3$ weight ratio from 2 to 9, a BET surface area from 250 to 500 m²/g and a Na content of less than 200 ppm, wherein the catalyst comprises a crystalline aluminosilicate zeolite and a binder, characterized in that the ratio of the peak heights of the IR absorption bands $v=3610$ cm$^{-1}$ ±20 cm$^{-1}$/$v=3680$ cm$^{-1}$ ±20 cm$^{-1}$ of the catalyst is greater than 1.8.

2. Catalyst according to claim 1, characterized in that the aluminosilicate zeolite has an MFI structure and the binder comprises aluminium oxide.

3. Catalyst according to claim 1, characterized in that the ratio of the peak heights of the IR absorption bands $v=3610$ cm$^{-1}$ ±20 cm$^{-1}$/$v=3680$ cm$^{-1}$ ±20 cm$^{-1}$ of the catalyst is 2.0 or greater.

4. The catalyst of claim 3 wherein the ratio of the peak height of the IR bands of the catalyst is between 2.1 and 3.0.

5. Catalyst according to claim 1, characterized in that the aluminosilicate zeolite is present in an H form.

6. Process for producing the catalyst according to claim 1, comprising the following steps:
   (a) crystallizing an aluminosilicate from an aqueous synthesis suspension, comprising a silicon source, an aluminium source, an alkali source and a template;
   (b) separating the aluminosilicate out of the synthesis suspension, followed by a drying step and a calcining step to remove the template from the aluminosilicate;
   (c) ion exchanging alkali ions contained in the aluminosilicate in an aqueous medium with a proton-containing substance or a substance that yields protons when heated, wherein the molar ratio of the protons of the proton-containing or proton-yielding substance to aluminium in the aluminosilicate is from 5:1 to 50:1, followed by a drying step;
   (d) mixing the ion-exchanged aluminosilicate from stage (c) with a binder to form a product;
   (e) shaping the product from stage (d); and
   (f) final calcining of the product from stage (e).

7. Process according to claim 6, wherein in step (c), the obtained ion-exchanged product is separated off, washed with water until the conductivity of the medium is less than 200 μS/cm, and then dried and subjected to an intermediate calcining.

8. Process for producing olefins from oxygenates selected from the group consisting of methanol, dimethyl ether or mixtures thereof, comprising conducting an educt gas over the catalyst of claim 1.

9. Process for oligomerizing olefins, comprising conducting an educt gas over the catalyst of claim 1.

* * * * *